US00PP31654P2

(12) United States Plant Patent
Ren et al.

(10) Patent No.: US PP31,654 P2
(45) Date of Patent: Apr. 14, 2020

(54) MUSCADINE GRAPE PLANT NAMED 'FLORIANA'

(50) Latin Name: ***Vitis rotundifolia* Michx.**
Varietal Denomination: Floriana

(71) Applicant: Florida A&M University, Tallahassee, FL (US)

(72) Inventors: Zhongbo Ren, Tallahassee, FL (US); Jiang Lu, Shanghai (CN); Violeta Tsolova, Tallahassee, FL (US)

(73) Assignee: Florida A&M University, Tallahassee, FL (US)

( * ) Notice: Subject to any disclaimer, the term of this patent is extended or adjusted under 35 U.S.C. 154(b) by 0 days.

(21) Appl. No.: 15/999,982

(22) Filed: Sep. 7, 2018

(51) Int. Cl.
*A01H 5/08* (2018.01)
*A01H 6/88* (2018.01)

(52) U.S. Cl.
USPC ..... Plt./206

(58) Field of Classification Search
USPC ..... Plt./205, 206
See application file for complete search history.

(56) References Cited

U.S. PATENT DOCUMENTS

PP4,771 P 9/1981 Fry
PP5,824 P 12/1986 Ison
PP7,266 P 7/1990 Ison
PP7,267 P 7/1990 Ison

*Primary Examiner* — Susan McCormick Ewoldt
(74) *Attorney, Agent, or Firm* — Steven M. Forte; Smith & Hopen, P.A.

(57) ABSTRACT

A new and distinct cultivar of the muscadine grape plant, *Vitis rotundifolia* Michx., which is self-fertile wine grape vine that is highly productive, resistant to Pierce's disease and low fruit ripening rot (ripe rot, and bitter rot), and able to produce fine red wines. The new and distinct cultivar produces a high-quality wine with rich stable red color and consistent yield. The cultivar has moderate-vigorous vine growth with high fruit yield. The cultivar produces wines with deep red color, smooth mouthfeel, excellent stability, and good longevity. The cultivar has hermaphroditic self-fertile flowers.

2 Drawing Sheets

FEDERALLY SPONSORED RESEARCH OR DEVELOPMENT

This research was supported by the Florida Department of Agriculture and Consumer Services.

Genus and species of new cultivar: *Vitis rotundifolia* Michx.

BACKGROUND OF THE INVENTION

Muscadine grape, *Vitis rotundifolia* Michx., is a substantial fruit crop in the southeastern United States, where the production of bunch grapes is limited by the lethal Pierce's Disease (*Xylella fastidiosa*), and other diseases prevailing with the hot and humid environment there. In the North Florida climate, muscadine fruits ripen in late August to early September. The berries vary from about 3 g to 15 g in size and their color ranges from bronze to black. When fully ripe, the berries on some previously existing cultivars such as 'Dixieland' (U.S. Plant Pat. No. 4,771) are generally bronze, but the berries on other preexisting cultivars can range from red to black with slightly raised lenticels, giving a somewhat mottled appearance.

Muscadine grapes have been grown for fresh market, juice, and wine, while wine grapes accounted for over 70% of the grapes produced. Commercial muscadine fine wines and port wines dating back to 16th century in and around St. Augustine, Fla. Today, vineyards throughout the southeastern United States produce numerous muscadine wines every year, which having a large influence on the economy. In Florida alone, the grape and wine industry has nearly a billion-dollar impact on the state's economy, and the industry is expanding, due to the rich phytopharmaceuticals qualities of the muscadine wines. Muscadine wines are made mainly with 'Carlos' (not patented) having white and 'Noble' having red grapes, which are highly accepted for their superior horticultural and premium wine qualities. Some wines are made with several other muscadine grapes, such as 'Doreen', (not patented) 'Pineapple', (not patented) 'Pride', (not patented) 'Regal', (not patented) 'Scuppernong', (not patented) and 'Welder', (not patented) but in small or experimental productions due to the limitations of the vine and/or wine profiles.

'Noble' was released in 1973 by W. Nesbitt, D. Carroll, and V. Underwood. It was selected from the cross 'Thomas' and 'Tarheel' for its potential as a high yielding wine and juice grape. 'Noble' is a self-fertile and non-patented grape and is the most popular red muscadine grape for premium red wine and good quality juice production. 'Noble' is highly productive, vigorous, and disease resistant with its purple pigments being more stable than most muscadines in which the pigment tends to brown over time. The fruit ripening of 'Nobel' is uniform having a less musky flavor than most muscadine grapes.

'Carlos' was released by W. B. Nesbitt, V. H. Underwood, and D. E. Carroll in 1970 and was selected in 1954 from the cross: Howard x NC 11-173 ('Topsail' and 'Tarheel'). 'Carlos' was released as a bronze juice and fresh market cultivar with a flavor similar to 'Scuppernong'. 'Carlos' represents most of the acreage of muscadine grapes grown in North Carolina today. 'Carlos' has excellent production potential and was a dual-use variety; it is the standard processing variety in muscadine grown regions and it is also acceptable for fresh local marketing, but it is not recommended for wholesale markets because of its smaller berry size. The dry scars and even ripening facilitate the use of mechanical harvesting techniques with 'Carlos'. The vines are healthy, and yields have been good, though some Pierce's disease symptoms are present on the vine leaves. The main problem of 'Carlos' is berry rot, which averaged 13.7% in harvested fruits. Additionally, yield and wine quality could similarly be reduced potentially with the problem.

'Pineapple' (U.S. Plant Pat. No. 7,266) was introduced in 1988 having a listed pedigree being 'Fry' and 'Senoia'. 'Pineapple' is an excellent bronze self-fertile variety that produced fruits medium-sized fruits weighted 8.5 g with 15.4% (SSC) sugar content with a unique hint of pineapple flavor. The vine vigor and yield are moderate and is disease resistant. This medium-sized fruit is likely too small for the commercial fresh grape market today, while the striking feature of this cultivar is that it has a pineapple flavor, even this is more a hint rather than a strong pineapple flavor, this feature could be valuable in muscadine grape cultivar improvement.

'Supreme' (U.S. Plant Pat. No. 7,267) is a muscadine grape cultivar introduced in the late 1980s for the fresh fruit market in the Southeastern United States. It was developed from a cross between the female variety 'Black Fry' (U.S. Plant Pat. No. 5,824) and the pollen parent 'Dixieland' made by Mr. W. G. Ison. 'Supreme's' distinguishing features were that it was an improved variety at the time of its release of the muscadine grape, and the large-sized black berry.

'Black Fry' (U.S. Plant Pat. No. 5,824) was developed from a cross between the female variety 'Fry' (unpatented) and the pollen parent variety 'Cowart' (not patented), also made by Mr. Ison. 'Black Fry's' distinguishing features were that its characteristics, such as quality, shelf life, and sugar content were superior to both parents.

Despite these distinguishing characteristics of 'Carlos' and 'Noble', customers are constantly looking for a variety with even better wine profiles and horticultural characteristics. Furthermore, we have noticed a lack of red color with 'Noble' wines, Pierce's disease, and fruit rot problems with 'Carlos' vines. Thus, there has been a need to develop a new cultivar with improved horticulture traits and better premium wine profiles, such as disease resistance, high yield, less fruit rot during ripening, distinguished flavor, and a rich and stable color for red wines.

BRIEF SUMMARY OF THE INVENTION

'Floriana' (*Vitis rotundifolia* Michx.) is a new muscadine cultivar bred for the red wine grape industries in Florida and the Southeastern United States. 'Floriana' is a self-fertile wine grape vine that is highly productive, resistant to Pierce's disease (PD) and low fruit ripening rot (ripe rot and bitter rot), and is able to produce fine red wines. The most outstanding characteristics of 'Floriana' are the high-quality wine produced having a rich and stable red color with and consistent high-yield.

The following traits have been repeatedly observed and are the most pronounced characteristics of this new cultivar when grown in Florida, and which in combination distinguish it from existing cultivars:

1) Moderate vigorous vine growth with high fruit yield and evident disease resistant.
2) Premium red wine producing muscadine variety.
3) Wines with deep red color, smooth mouthfeel, excellent stability, and good longevity.
4) Hermaphroditic self-fertile flowers.

BRIEF DESCRIPTION OF THE DRAWINGS

The accompanying color photographs show a representative section of a typical specimen of the new cultivar.

DETAILED BOTANICAL DESCRIPTION

Figure 1:
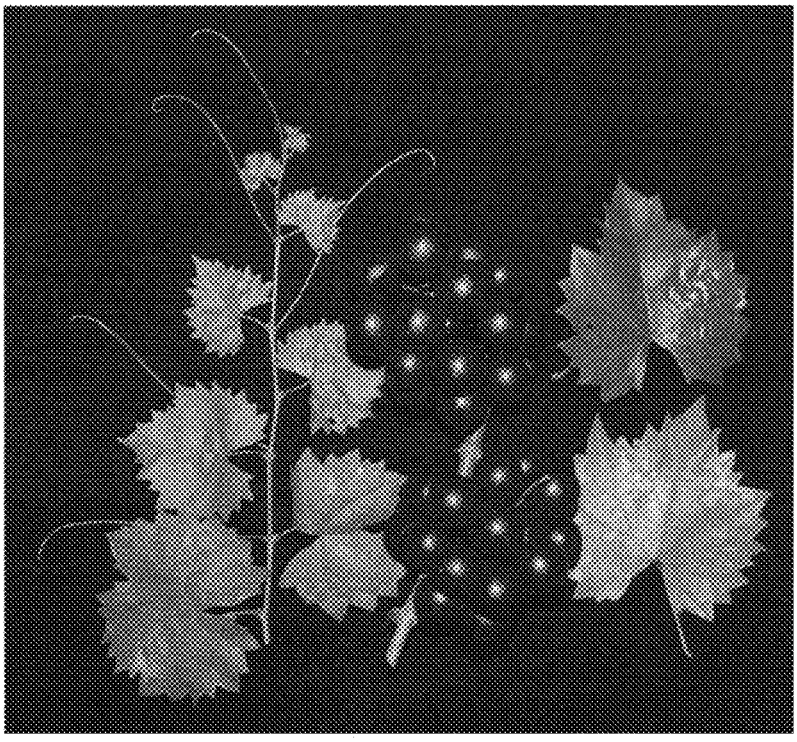
FIG. 1 is a detailed view of several clusters of ripe berries, shoot tips, and leaves of a 12-year-old plant.

In the following description, color references are made as per *The Royal Horticultural Society Colour Chart* (R.H.S.), The Royal Horticultural Society, London, 2015 (sixth edition) except where general terms of ordinary dictionary significance are used.

Origin of the Cultivar

'Floriana' was developed under the grape breeding program and asexually reproduced from cuttings taken from the original seedling at the Center for Viticulture and Small Fruit Research, Florida A&M University (FAMU), 6361 Mahan Drive, Tallahassee, Fla. 32308. 'Floriana' originated from a seedling population crossed between *Vitis rolundifolia* Michx. cultivars 'Supreme' (U.S. Plant Pat. No. 7,267) and 'Pineapple' (U.S. Plant Pat. No. 7,266) in 1999. The seedling was selected from a progeny of 243, and testing of the agronomic characteristics began in 2006 in Tallahassee, Fla. The new cultivar has been tested under the experimental designation "O28-22-5" or "C16-6." The unique features of the new cultivar have been retained.

The first wine was made with 23.6 kg fruits from the single original hybrid vine in 2006. The propagated vines were planted 12 feet between the rows and 20 feet within the rows and trained to single-wire two-arm cordons. A 4-5 bud spur pruning system was applied in winter pruning with minimal green canopy management. The vineyard was maintained according to the standard vineyard management system for muscadine grapes having adequate irrigation, fertilization, and minimal chemical protection. Wines were made regarding established protocols by the Center's vinification research and evaluated utilizing taste panels during the annual meetings of the Florida Wine Grape Growers Association (FWGGA) according to the American Wine Society (AWS) evaluation standards utilizing a total 20-point scoring system based on appearance (0~3), aroma/bouquet (0~6), taste/texture (0~6), after taste (0~3) and overall impression (0~2).

Color stability was monitored with aging wines at 1st and 5th years after vinification, their absorbance at 420 nm and 520 nm were recorded with Genesys 10 uv spectrophotometer; samples were diluted 10× times with ddH2O, and 10 mm crystal curettes were used.

Methods of Asexual Reproduction

'Floriana' was asexually reproduced in research vineyards, utilizing standard mist propagation techniques. Soft wood cuttings from the original 'Floriana' vine was taken from June through August, the basses of the two-node softwood cuttings were first dip-touched briefly with Hormodin-3 root inducing substance (OHP, Inc., PO Box 230, Mainland, Pa.), placed in a 50% sand and 50% peat moss medium, and kept in mist screen house. They were misted for 30 seconds in 10-minute intervals for a period of about 10 hours during the day. After rooting in five or more weeks, the cuttings were transferred into 0.5-gallon pots with potting soil and moved out of the mist bed to a shaded nursery for further developing. Another method of asexual reproduction is layering during later summer through mid-fall, wherein the current season's growth is placed into a trench 20 cm deep at the base of the mother plant, still attached to the mother vine, and covered with soil. Rooting cuttings from the material in the trench can then be separated from the mother plant during the following dormant season, laying may be 100% rooting proof.

'Floriana' originated from a seedling population crossed between the female parent *Vitis rolundifolia* Michx. cultivars 'Supreme' (U.S. Plant Pat. No. 7,267) and the male parent 'Pineapple' (U.S. Plant Pat. No. 7,266) in 1999. The seedling was selected from a progeny of 243, and testing of the agronomic characteristics began in 2006 in Tallahassee, Fla. The new cultivar was asexually reproduced from cuttings taken from the original seedling and the new cultivar has been tested under the experimental designation "O28-22-5" or "C16-6." The unique features of the new cultivar have been retained.

Plant Characteristics

The following plant characteristics are relevant for plants that are five years old. Muscadine vines grown from seed will normally take three years to bloom and set fruits. The vine reaches peak production in four to five years. Commercially grown vines are produced by asexual clonal propagation, from rooted cuttings of the annual growing soft shoots. They can bloom and set fruits in the second year after planting and will reach full fruit production in three to four years.

Vine

The vines of 'Floriana' grow moderately, i.e., the growth of lateral canes on mature vines is about 1.2 to 2.4 m per growing season, weak-moderate vigor could be noticed with the over cropped vines. The vines typically fill a 3.6 m single-wire trellis in the second growing season in Florida. The pruning weight of mature 'Floriana' is about ⅓ of 'Carlos' and ½ of 'Noble' (standard muscadine grape wine cultivars). Typical five-year-old vine of 'Floriana' cultivar has a smooth and compact texture, with non-shedding bark with browning gray color (RHS N200C) and trunk caliper measurement at 30 cm above the soil line averages 3.1 cm.

Shoots

The young 'Floriana' shoots are deep greenish-yellow (RHS 153A), and mature shoots are greyish reddish orange (RHS 177C) with average 3.9 cm internodes and 5.1 mm in diameter. Shoots grow horizontally to semi-droopingly and generally grow 1.2 to 2.0 m or more in a growing season in North Florida. New shoots from dormant buds typically produce inflorescences at the 3rd and 4th nodes. Inflorescences are compound panicles composed of 10 to 20 flower clusters, each containing 5 to 15 individual female flowers. Tendrils are unbranched, averaged 15 cm in length and 1.8 mm in diameter, and the pith discontinuous along the nodes.

Buds

The development of shoots in the spring results from the emergence of compound buds on the canes. Each bud arises as an axillary bud meristem in each leaf axil of the shoot in the previous growing season. Potential fruiting clusters, also called inflorescences, are initiated within developing axillary buds the season prior to bloom. The inflorescences may be up to 10 cm long at bloom. The inflorescence is a panicle consisting of flowers arranged within variously branched dichasia. Thus, the main axis is terminated by a flower, as are each of the lateral branches. The flowers start to bloom in late mid-May and are at full bloom in late May to early June.

Foliage

Figure 2:
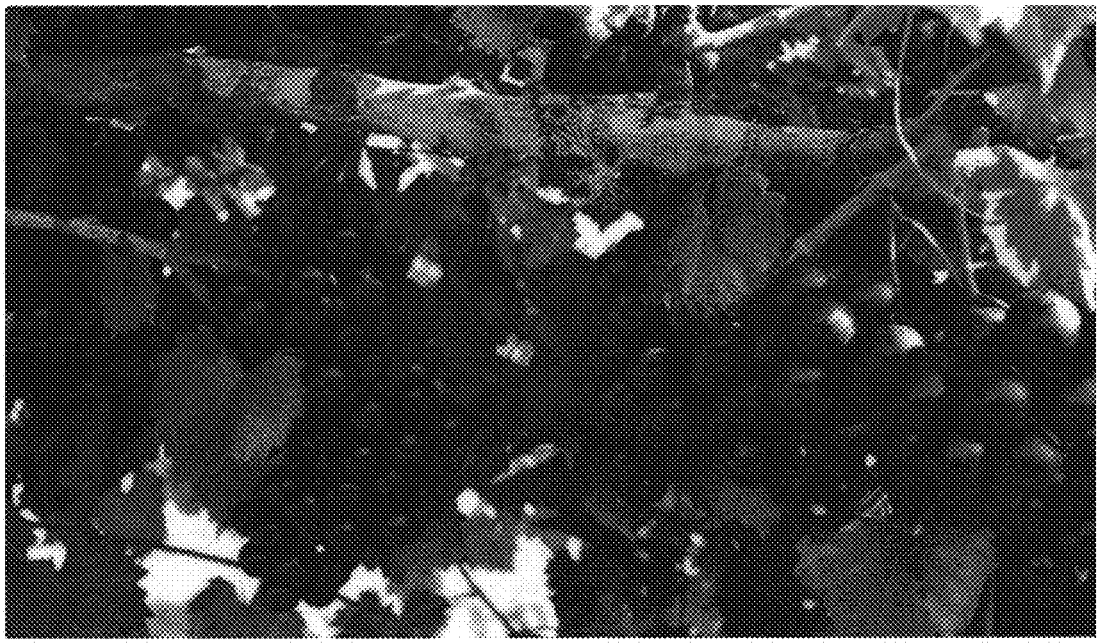
FIG. 2 is a perspective view of several clusters of ripe berries on the vine in fruit maturity of a 12-year-old plant.

'Floriana' has ~8 cm mid-sized, round, unlobed leaves with 20-30 dentate margins and an acuminate point. Leaves average 7.7 cm in length and 7.8 cm in width. The leaves are nearly circular with broadly toothed margins and glabrous on both upper and lower surfaces. The venation pattern is netted or reticular having a vein color of moderate olive brown (RHS 199A) Mature upper leaf surface is moderate olive green (RHS 137A) and somewhat shiny, while the lower leaf surfaces are moderate yellow green (RHS 137C) and are not as dark and less bright compared to the upper surface. The leaves become subglabrous at maturity and are deciduous. Petiole length equals or slightly short the blade midrib length and the petiole sinus is half opened. The average petiole is about 5.1 cm long and 2 mm in diameter (FIGS. 1 and 2) with a petiole color of moderate olive brown (RHS 199A).

Flowers

'Floriana' bears hermaphroditic flowers, or it is self-fertile, which do not require pollinators to set fruits. Flower are small with unopened flowers at blooming being 2.5 mm in diameter and 2 mm in ovary diameters in open flowers. The flowers are indiscrete, and moderate yellow green (RHS 138C), borne in racemose panicles opposite leaves at the base of current season's growth.

The anthers are light yellow green (RHS 2D), and supported on erect filaments at the base of the ovary. The flowers are short-lived, lasting approximately 3 to 5 days. 'Floriana' typically blooms from later May to early June at Tallahassee, Fla. There are 5 each of sepals, petals, and stamens in brilliant yellow green (RHS 150C). Ovaries are superior and contain 2 locules each with 2 ovules. Each cluster has about 10-30 flowers. The calyptera, or cap is the corolla, in which the petals are fused at the apex; it abscises at the base of the flower and pops off at anthesis. No capping symptoms has been observed yet.

'Floriana' is self-fertile and no pollinator is needed.

Fruits

The vines produce small-medium sized dark-red fruits, which ripen evenly in early to mid-September in Tallahassee, Fla. At maturity, the berries weigh average 5.3 g and 15.8% soluble solids (SSC). The berries have typical muscadine aromatic flavor and relative thick skins, but no-colored flesh. The berries are round to slightly elongated with a length or height (L) of 1.96 cm and diameter (D) of 1.92 cm providing a 1.02 length to diameter (L/D) ratio. Each of the berries contains 3.6 seeds on average. The fruit is borne in dense clusters of 8-36 grapes (average 15.1 berries per cluster). The berries have inconspicuous lenticels giving them a relatively smooth dark red appearance. The berries separate from the pedicel with a relatively low wet scar, i.e., more than 80% of the berries are torn at the point of detachment from the pedicel. The black red color of the 'Floriana' fruit falls into the dark grayish purple group (RHS N92A). This fruit color is distinct from the bronze fruit of 'Carlos' and the black to deep red color of 'Noble'. A comparison of the 'Floriana' horticultural characteristics (size, soluble solids, berry, yield, etc.) and overall wine profiles are presented in Table 1 and Table 2, these observations have been made annually over a three year period, and the traits have been retained.

Disease/Pest Resistance or Susceptibility

Like most of the muscadine grapes, 'Floriana' exhibit greater disease tolerance than other American native and European origin grapes. It is highly disease tolerant and practically immune to phylloxera, nematodes, and Pierce's disease with very low fruit rot and relatively low wet scar. No severe fungal diseases have been observed except slight leaf spot late in the season.

Ripening rot which including but not limited to Bitter Rot (pathogen *Greeneria uvicola*), Ripe Rot (pathogen *Colletotrichum* sp.), and Macrophoma Rot (pathogen *Botryosphaeria dothidea*), is 3.6% on average, similar to that of 'Noble', while much lower than that of 'Carlos' (Table 1).

TABLE 1

Horticultural characteristics of 'Floriana' and leading wine muscadine cultivars in Tallahassee, FL

| | flower type | vigor | node length (cm) | node circle (cm) | leaf size (L × W) (cm) | pruning weight (kg) |
|---|---|---|---|---|---|---|
| Carlos | perfect | v. vigor | 4.4 | 2.0 | 9.0 × 8.4 | 10.0 |
| Noble | perfect | vigor | 4.4 | 2.0 | 8.9 × 8.9 | 5.9 |
| Floriana | perfect | m. vigor | 3.7 | 1.5 | 8.5 × 8.6 | 2.7 |

TABLE 1-continued

Horticultural characteristics of 'Floriana' and leading wine muscadine cultivars in Tallahassee, FL

| | PD (0-5) | cluster/ spur | cluster/ shoot | fruit/ cluster | yield (kg/ vine) | dry scar (%) | harvest fruit rot (%) |
|---|---|---|---|---|---|---|---|
| Carlos | 1 | 4.2 | 2.1 | 14.4 | 29.1 | 13.7 | 1 |
| Noble | 0 | 2.7 | 1.3 | 15.8 | 25.6 | 3.5 | 0 |
| Floriana | 0 | 2.6 | 1.4 | 15.1 | 26.7 | 3.6 | 0 |

TABLE 2

Fruit and wine characteristics of 'Floriana' and premium wine muscadine cultivars in Tallahassee, FL

| | Color | Size (g) | SSC (%) | TA (%) | pH | Wine Score (0-20) |
|---|---|---|---|---|---|---|
| Carlos | Bronze | 5.7 | 15.2 | 0.411 | 3.13 | 13.9 |
| Nobel | black red | 3.2 | 16.3 | 0.441 | 3.49 | 12.7 |
| Floriana | black red | 5.3 | 15.8 | 0.416 | 3.36 | 13.2 |

| | Wine color development | | | |
|---|---|---|---|---|
| | 520 nm absorbance | | Hue (420/520 nm) | |
| | 1 year | 5 year | 1 year | 5 year |
| Carlos | — | — | — | — |
| Nobel | 0.159 | 0.105 | 0.795 | 1.637 |
| Floriana | 0.191 | 0.158 | 0.807 | 1.129 |

What is claimed is:

1. A new and distinct variety of muscadine grape plant named 'Floriana', substantially as herein described and illustrated.

* * * * *